(12) United States Patent
van Krieken

(10) Patent No.: US 7,223,885 B2
(45) Date of Patent: May 29, 2007

(54) METHOD FOR THE PURIFICATION OF A-HYDROXY ACIDS ON AN INDUSTRIAL SCALE

(75) Inventor: Jan van Krieken, Gorinchem (NL)

(73) Assignee: Purac Biochem B.V., Gorinchem (NL)

( * ) Notice: Subject to any disclaimer, the term of this patent is extended or adjusted under 35 U.S.C. 154(b) by 431 days.

(21) Appl. No.: 10/380,706

(22) PCT Filed: Sep. 14, 2001

(86) PCT No.: PCT/NL01/00682

§ 371 (c)(1),
(2), (4) Date: Jan. 12, 2004

(87) PCT Pub. No.: WO02/22544

PCT Pub. Date: Mar. 21, 2002

(65) Prior Publication Data

US 2004/0249206 A1    Dec. 9, 2004

(30) Foreign Application Priority Data

Sep. 15, 2000 (NL) .................................. 1016203

(51) Int. Cl.
*C07C 51/42* (2006.01)
*C07C 59/08* (2006.01)

(52) U.S. Cl. ....................................... 562/580; 562/589

(58) Field of Classification Search ................ 562/589, 562/580
See application file for complete search history.

(56) References Cited

U.S. PATENT DOCUMENTS 5,510,526 A    4/1996    Baniel et al.
5,859,296 A    1/1999    Neuamann et al.

FOREIGN PATENT DOCUMENTS

| DE | 593657 | 2/1934 |
| WO | WO 92/05138 | 4/1992 |
| WO | WO 00/56693 | 9/2000 |
| WO | WO 02/22544 A1 | 9/2001 |

OTHER PUBLICATIONS

L. B. Lockwood, et al., "Lactic Acid", Chemistry and Enzymology of Lactate Isomers, Jul. 31, 1965, pp. 654-657.
W.G. Kerckhoff, "The preparation of Crystalline Lactic Acid", Jun. 7, 1933, pp. 449-460.

*Primary Examiner*—Taylor Victor Oh
(74) *Attorney, Agent, or Firm*—Gilberto M. Villacorta; Sunit Talapatra; Foley & Lardner LLP

(57) ABSTRACT

The present invention relates to a method for the purification of an α-hydroxy acid on an industrial scale, in which an α-hydroxy acid with a color (fresh) of not more than 10,000 APHA units is subjected to (a) a crystallization step followed by (b) a distillation step.

12 Claims, No Drawings

METHOD FOR THE PURIFICATION OF A-HYDROXY ACIDS ON AN INDUSTRIAL SCALE

The present invention relates to a method for the purification of α-hydroxy acids, in particular lactic acid or glycolic acid, on an industrial scale, as well as to products of the utmost chiral purity which can be obtained by this method, and to applications thereof.

Lactic acid is usually marketed as a dilute or concentrated solution, because lactic acid has a strong tendency to form intermolecular esters (dimeric and polymeric lactic acid). In addition, lactic acid (even very pure lactic acid) is strongly hygroscopic. The purification of lactic acid (the racemic mixture and in particular the enantiomers of lactic acid) on an industrial scale is a complicated and difficult process according to the prior art.

It is known how to produce lactic acid, or 2-hydroxypropionic acid, in a fermentative manner. In general the fermentative production of lactic acid includes first of all a fermentation step in which a carbohydrate-containing substrate such as glucose or sucrose is converted to lactic acid by a suitable microorganism. Known microorganisms producing (S)-lactic acid are various bacteria of the genus *Lactobacillus,* such as *Lactobacillus casei* for example. In addition microorganisms are also known which produce R-lactic acid selectively. The aqueous fermentation product is then processed in order to obtain lactic acid. The usual industrial processing path generally consists of separation of the biomass followed by acidification, purification and concentration.

In the case of (S)-lactic acid the lactic acid so obtained is sufficiently pure to be processed in foods for human consumption. (S)- or (R)-lactic acid which is ultimately obtained by this usual method can be 98% enantiomerically pure or even higher (i.e. 98% or more of the lactic acid present consists of the (S) or (R) enantiomer). The product still contains residual sugars, however. The product is also yellow in colour and on heating this becomes brown to black through decomposition of impurities. Moreover, in the case of S-lactic acid, the organoleptic properties often leave something to be desired. The lactic acid enantiomer is thus moderately suitable for application in foods, but on the whole not suitable for pharmaceutical applications and for synthesis of chiral compounds.

The purity of the product can be increased by esterification followed by hydrolysis, so that it is suitable for pharmaceutical applications. As a result of this esterification/hydrolysis, however, the enantiomeric purity decreases and the lactic acid still contains a small amount of the alcohol which has been used in the esterification. Examples of other methods for the purification of lactic acid include subjecting aqueous solutions of lactic acid to one or more extraction, (steam) distillation and/or evaporation steps, electrodialysis steps and crystallizations (see for example Ullmans Encyklopädie der Technischen Chemie, Verlag Chemie GmbH, Weinheim, fourth edition, Part 17, pages 1–7 (1979); H. Benninga, "History of Lactic Acid Making", Kluwer Academic Publishers, Dordrecht-Boston-London (1990); C. H. Holten, "Lactic Acid; Properties and Chemistry of Lactic Acid and Derivatives", Verlag Chemie GmbH, Weinheim (1971); The Merck Index, Merck & Co., Inc., eleventh edition, page 842 (1989); Römmp Chemie Lexicon, G. Thieme Verlag, Stuttgart and New York, ninth edition, Part 4, pages 2792–2893 (1991) and the Netherlands patent applications 1013265 and 1013682.

In German Patent 593,657 (granted on 15 Feb. 1934) a laboratory experiment is described in which an aqueous solution of lactic acid, which contained an excess of the S component and practically no lactic acid anhydride, was concentrated by means of a thin-film evaporation technique, if necessary at reduced pressure. The concentrated lactic acid solution was then rapidly cooled, with formation of crystals. After that the crystals were separated from the mother liquor, washed with ether and repeatedly recrystallized from ethyl acetate or chloroform or a comparable solvent until the crystals showed a sharp melting point of 53° C. The chiral purity or the enantiomeric excess and the colour are not reported.

In H. Borsook, H. M. Huffman, Y-P. Liu, J. Biol. Chem. 102, 449–460 (1933) a laboratory experiment is described in which an aqueous mixture, which contained 50 percent lactic acid with an excess of S-lactic acid, 30 percent lactic acid anhydride and lactic acid dimer and 15 percent water, was subjected to fractional distillation at approximately 0.13 mbar and 105° C. The middle fraction was then distilled again and after that cooled in an ice/salt bath with formation of a solid crystal mass. It is reported that the distillation has to be performed with small quantities, because with larger quantities there is a big loss of product as a result of the long heating time. The solid crystal mass was then recrystallized three times from an equal volume of equal quantities of diethyl ether and diisopropyl ether, and the crystals were isolated and dried at room temperature in a vacuum drier. In this way it was possible to obtain (S)-lactic acid with a melting point of 52.7–52.8° C. which contained less than 0.1 percent impurities such as water, lactic acid anhydride or lactic acid dimer. The chiral purity or the enantiomeric excess and the colour of S-lactic acid are not reported.

In L. B. Lockwood, D. E. Yoder, M. Ziemy, Ann. N.Y. Acad. Sci. 119, 854 (1965) the distillation and crystallization of lactic acid on a laboratory scale is also described, the melting point of the optically pure lactic acid obtained being 54° C. The colour is not reported.

In 1934 the crystallization of lactic acid was investigated by Boehringer Ingelheim, but this method was not found to give good results, owing to problems with the purification and further treatment. After the Second World War, however, it turned out that Boehringer Ingelheim was able to produce lactic acid for pharmaceutical applications on a scale of about 12 to 15 tons per month, with a yield of about 77 to 86 percent. In this process an aqueous solution of lactic acid was purified by means of steam distillation at reduced pressure (about 13 mbar), followed by crystallization at −25° C., after which the crystals were dissolved in water and the solution was treated with potassium ferrocyanide (to remove heavy metals) and activated charcoal. The chiral purity or the enantiomeric excess or other properties such as colour and odour of the S-lactic acid so produced are not known (see H. Benninga, "History of Lactic Acid Making", Kluwer Academic Publishers, Dordrecht-Boston-London, pages 347–350 (1990)).

Crystalline (S)-lactic acid has been marketed by, for example, Fluka and Sigma with purities of more than 99% (see for example M. L. Buszko, E. R. Andrew, Mol. Phys. 76, 83–87 (1992) and T. S. Ing, A. W. Yu, V. Nagaraja, N. A. Amin, S. Ayache, V. C. Gandhi, J. T. Daugirdas, Int. J. Artif. Organs 17, 70–73 (1994)). Crystalline S-lactic acid with a water content of less than 1 percent by weight is known from EP A 563,455 (see Example 1). The crystal structure of lactic acid is described in A. Schouten, J. A. Kanters, J. van Krieken, J. Mol. Struct. 323, 165–168 (1994).

Lactic acid can also be obtained in a synthetic manner. This is known. The product of the synthetic production method, however, is a racemic mixture which thus contains (S)-lactic acid and (R)-lactic acid in equal quantities. It is true that the separate enantiomers can be separated by means of known techniques, such as diastereoisomer separation techniques, where one of the enantiomers crystallizes out as a salt and this salt is then converted back to the enantiomeric lactic acid, but the enantiomeric product finally obtained will inevitably still contain significant quantities of the other enantiomer.

In European Patent Application 552,255 it is reported that glycolic acid of industrial quality can be crystallized by putting a solution thereof in a freezer, giving rise to crystals which are filtered off. It will be clear that such a method is unsuitable for being carried out on an industrial scale. Such a method is also applied in DE A 2,810,975.

In WO 00/56693 a method is described for the purification of lactic acid on an industrial scale, the method involving: (a) the distillation under reduced pressure of a concentrated lactic acid solution with a total acid content of at least 95% by weight and a monomeric lactic acid content of at least 80% by weight, calculated in terms of the concentrated lactic acid solution, and with a ratio of the lactic acid enantiomers not equal to 1, and (b) subjecting the distilled lactic acid solution to a crystallization, with formation of pure lactic acid, where the pure lactic acid has a total acid content of at least 99% by weight, a monomeric lactic acid content of at least 98% by weight, a chiral purity of 99% or more, calculated in terms of the total quantity of pure lactic acid, a colour of not more than 10 APHA units and an acceptable odour.

Disadvantages of the method according to WO 00/56693 are that the yield, although not low in relative terms, can be improved, that the method requires a great deal of energy and that a relatively large quantity of acid has to be distilled.

The present invention aims to solve these problems and therefore relates to a method for the purification of an α-hydroxy acid on an industrial scale (i.e. a scale of at least 1000 tons per annum), in which an α-hydroxy acid with a colour (fresh) of not more than 10,000 APHA units is subjected to (a) a crystallization step followed by (b) a distillation step.

It will be clear to an expert that the method according to the invention can comprise two or more crystallization steps and/or two or more distillation steps. According to the invention, however, it is preferable for only one crystallization step to be performed, because otherwise the energy advantage would be less.

Advantages of the method according to the invention are a relatively low energy consumption. This is mainly due to the fact that during the crystallization a relatively large amount of impurities are removed and a product is obtained which contains little water, generally less than 1% by weight, calculated in terms of the whole product, so that this can be easily distilled (after only melting). Moreover, the quantity of feed which has to be distilled for an equal quantity of end product is much smaller.

An α-hydroxy acid means a carbonic acid which is substituted with a hydroxy group on the α carbon atom. The general formula of an α-hydroxy acid is therefore:

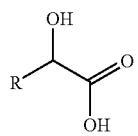

where R is a hydrogen atom, a $C_1$–$C_5$ alkyl group (preferably a methyl group), a $C_6$–$C_{12}$ aryl group or a heterocyclic cycloalkyl or -aryl group. The α-hydroxy acid according to the invention is preferably lactic acid (R is methyl) or glycolic acid (R is hydrogen) and is in particular lactic acid.

The feed for the method is preferably characterized by a colour (fresh) of not more than 7500 APHA and in particular of not more than 5000 APHA, a total acid content of at least 70% by weight, relative to the whole feed, and a free acid content of at least 60% by weight, relative to the whole feed. If the α-hydroxy acid is lactic acid, the feed preferably has a total acid content of at least 80% by weight and a free acid content of at least 70% by weight. The feed is further characterized by a total nitrogen content of not more than 10,000 ppm, preferably not more than 5,000 ppm, and a total quantity of residual sugars (predominantly polysaccharides) of not more than 20,000 ppm, preferably not more than 10,000 ppm, where all the contents here indicated are relative to the whole feed. The chiral purity of the feed, if applicable, is at least 90% and preferably at least 95%.

Total acid content (TA) is the acid content after saponification of intermolecular ester bonds with an excess base and is determined by back titration with acid. The total acid content thus gives the quantity of monomeric, dimeric and polymeric lactic acid. The free acid content (FA) is determined by direct titration with base, i.e. before saponification of the intermolecular ester groups. The content of monomeric lactic acid (MM) is here defined as:

$$MM = TA - 2 \times (TA - FA)$$

provided that TA−FA<10%. This means that not very much dimeric or polymeric lactic acid can be present. It is also assumed that the non-monomeric lactic acid is present in the form of lactoyl lactic acid (dimer).

Chiral purity (for an excess (S)-isomer) is here defined as:

$$\text{Chiral purity} = 100\% \times \{((S)\text{-isomer})/((R)\text{-isomer} + (S)\text{-isomer})\}$$

The known crystallization techniques can in principle be applied in the method according to the present invention. An example of such a technique is melting crystallization (or cooling crystallization), where the condensed, liquid concentrate or distillate, which for example contains (S)- or (R)-lactic acid in a molten state, is directly cooled, so that the (S)- or (R)-lactic acid crystallizes out. It is preferable to keep the temperature at which crystallization occurs (the crystallization temperature) as low as possible, so that the formation of oligomers and polymers of the α-hydroxy acid is limited as much as possible. According to the invention a concentrate is preferably used, since the preparation of a distillate is unfavourable in terms of process energy.

Melting crystallization is a process in which a crystalline material is obtained from a melt of the material to be crystallized. This technique is for example described in detail in Kirk-Othmer, Encyclopedia of Chemical Technology, fourth edition, Part 7, pages 723–727 (1993), in J. W. Mullin, "Crystallization", third revised edition, Butterworth-Heinemann Ltd., pages 309–323 (1993) and in J. Ullrich and B. Kallies, Current Topics in Crystal Growth Research, 1 (1994), which have been recorded here for reference. The main advantage of melting crystallization relative to distillation is that much less energy is needed, because the enthalpy of melting of organic compounds is generally lower than the enthalpy of evaporation. This advantage also occurs with other crystallization techniques, because the enthalpy of crystallization is usually lower than the enthalpy of evaporation. Another advantage of melting crystallization relative to distillation is furthermore that the process can generally be carried out at a much lower temperature—which is advantageous when the organic compound is thermally unstable.

The melting crystallization can be carried out with the aid of a suspension crystallization or a layer crystallization, if necessary in combination with a washing column or a centrifuge, or another purification technique. Examples of suitable equipment and processes are described in Kirk-Othmer, Encyclopedia of Chemical Technology, fourth edition, Part 7, pages 723–727 (1993), in J. W. Mullin, "Crystallization", third revised edition, Butterworth-Heinemann Ltd., pages 309–323 (1993) and J. Ullrich and B. Kallies, Current Topics in Crystal Growth Research, 1 (1994), the content of which has been recorded here for reference.

It has also been found that crystallization of an aqueous solution gives very good results. In this crystallization treatment a concentrated lactic acid solution is for example diluted with water and this is then subjected to one or more cooling and/or evaporative crystallization steps. In these techniques the concentrate or distillate is directly cooled (cooling crystallization) or concentrated by evaporation of water (evaporative crystallization). The driving force for the crystallization in the cooling crystallization technique is the bringing about of supersaturation in the concentrated lactic acid solution by reducing the temperature of the concentrated lactic acid solution. As a result of the lower temperature of the solution the solubility decreases and supersaturation occurs.

The driving force for the crystallization in the evaporative crystallization technique is the bringing about of supersaturation in, for example, a concentrated lactic acid solution by evaporation of water, for which heat must be supplied in order to keep the temperature of the concentrated lactic acid solution constant. The heat of crystallization is thus effectively removed by cooling and evaporation of water, respectively. Crystallization of the lactic acid then occurs during the cooling and evaporation of water, respectively.

Another highly suitable crystallization technique is adiabatic crystallization, where the driving force for crystallization is the bringing about of supersaturation in, for example, a concentrated lactic acid solution by evaporation of water without supplying heat. The evaporation of water has two effects: (a) the temperature of the concentrated lactic acid solution becomes lower and (b) the concentration of the acid increases. Both effects lead to a decrease in the solubility and an increase in the supersaturation.

The crystallization steps are preferably carried out according to the invention by means of adiabatic crystallization or cooling crystallization, in particular by means of adiabatic crystallization. Seed crystals are preferably added to feed in the crystallizations. If a solvent is used in the crystallization, this is preferably water.

The α-hydroxy acid which is crystallized out can then be separated by the known methods for solid-liquid separation from the remaining liquid, or mother liquor.

Examples of suitable separation techniques for separating the α-hydroxy acid crystals from the mother liquor are centrifugation, decanting, filtration, separation by means of one or more washing columns, or a combination of two or more of these techniques. In the context of the invention it has been found that centrifugation and separation with one or more washing columns is particularly appropriate.

The mother liquors which are obtained still contain considerable quantities of α-hydroxy acid. For optimal process management it is therefore preferable to feed these mother liquors back into the process.

The distillation step is carried out under reduced pressure, using an α-hydroxy acid with a total acid content of at least 95% by weight, a monomeric α-hydroxy acid content of at least 80% by weight and a water content of at most 2% by weight, calculated in terms of the α-hydroxy acid. The ratio between the α-hydroxy acid enantiomers, if applicable, is preferably not equal to 1.

In the distillation according to the invention an α-hydroxy acid is formed with a total acid content of at least 98% by weight, preferably at least 99% by weight, where α-hydroxy acid contains at least 95% by weight monomeric α-hydroxy acid, calculated in terms of the lactic acid concentrate, and a distillation residue. The distilled α-hydroxy acid preferably contains at least 98.5% by weight monomeric α-hydroxy acid. The chiral purity of the α-hydroxy acid, if applicable, is preferably 90% or higher, more preferably 95% or higher, and in particular 99% or higher.

In the context of the invention "reduced pressure" means a pressure in the range from 0.1 to 20 mbar, in particular from 0.2 to 10 mbar. The temperature during the distillation under reduced pressure is preferably 100 to 200° C., in particular 110 to 140° C.

Impurities with a high boiling point are removed by the distillation under reduced pressure, because the α-hydroxy acid is obtained as the top product. According to the invention this distillation under reduced pressure is carried out in particular with the aid of a short-path distiller. The distillation under reduced pressure can also be carried out at a pressure of 0.1 to 20 mbar, in particular of 2 to 10 mbar, and at a temperature of 100° to 200° C., in particular a temperature of 110° to 140° C., where the α-hydroxy acid is preferably brought into the vapour phase by means of film evaporation, after which the vapour is conveyed to a distillation column. In this process, separation into two fractions takes place under reflux, with the top product containing at least 98% by weight total acid, preferably at least 99% by weight, and the residue containing residual sugars and polymeric α-hydroxy acid. The top product contains at least 95% by weight monomeric α-hydroxy acid, calculated in terms of the α-hydroxy acid concentrate. The top product preferably contains at least 99.5% by weight monomeric α-hydroxy acid. The chiral purity of this top product is preferably 90% or higher, more preferably 95% or higher, and in particular 99% or higher. According to this preferred embodiment the film evaporation preferably takes place by means of smeared film evaporation, thin-film evaporation and/or falling-film evaporation, with the distillation column or columns having a plate number from 1 to 10. Distillation step (a) ensures that α-hydroxy acid is separated from components such as residual sugars and polymeric α-hydroxy acid and components which give a colour to the impure α-hydroxy acid. These components or contaminants have a boiling point which is higher than that of α-hydroxy acid.

After isolation, the α-hydroxy acid which is obtained by the method according to the present invention is directly dissolved in a suitable solvent, usually water, in order to prevent coagulation of the hygroscopic α-hydroxy acid occurring. The concentration of the α-hydroxy acid solution so obtained can in principle have any desired concentration. In practice this will usually vary from 30 to 95%. Concentrations commonly occurring on the market are 80–90%.

The invention also relates to an α-hydroxy acid or an α-hydroxy acid solution with a chiral purity of at least 99% and a colour of not more than 10 APHA units, with the α-hydroxy acid or the α-hydroxy acid solution having an acceptable odour, in particular for pharmaceutical applications. In the case of an α-hydroxy acid solution the solvent is preferably water. The chiral purity is preferably at least 99%, in particular at least 99.5%, which corresponds to 99% enantiomeric excess (ee) or higher. Most preferable is chiral α-hydroxy acid, or the solution thereof, whose chiral purity is at least 99.8% (i.e. at least 99.6% ee).

The α-hydroxy acid or the α-hydroxy acid solution also meets the following requirements:
- alcohol content: not more than 250 ppm (alcohol is methanol, ethanol or other alcohol, as alcohol as such or in the form of a lactate).
- total nitrogen: not more than 5 ppm.
- total sugar: not more than 100 ppm.
- total polysaccharides: not more than 100 ppm.
- organic acids (other than lactic acid): not more than 250 ppm.

With regard to odour the α-hydroxy acid or the α-hydroxy acid solution possesses a considerable improvement for application in foods and a higher chemical purity than the products according to the prior art.

When it is chiral, the α-hydroxy acid according to the invention can be both an S-α-hydroxy acid and an (R)-α-hydroxy acid, depending on the microorganism which is used in the fermentation.

Because of their high chiral purity both the (S)-α-hydroxy acid and the (R)-α-hydroxy acid or the solutions thereof can very suitably be applied for chiral syntheses. The chirally pure (S)-α-hydroxy acid or solutions thereof are also very suitable for being applied in pharmaceutical preparations.

The invention therefore also relates to a pharmaceutical preparation which contains the (S)-α-hydroxy acid or the (S)-α-hydroxy acid solution described above. The invention is now illustrated by means of the following example.

EXAMPLE (S)-lactic acid with the following properties is used as the starting material:

| | |
|---|---|
| Total acid content | 95.4% |
| Free acid content | 91.1% |
| Colour (fresh) | 4850 APHA |
| Total nitrogen | 1080 ppm |
| Total residual sugars | 6490 ppm |
| Chiral purity | 99.61% |

In a first crystallization step a double-walled 2.7-liter vessel was connected with a thermostat bath and 2045 g of the starting material described above was put into the vessel. The acid was cooled to 40° C. while stirring and inoculated with 0.4 g of a suspension which contained seed crystals. The acid was then cooled from 40° to 30° C. in 5 hours in accordance with a linear cooling programme. The crystals formed were rod-shaped and many small particles were formed. After 5 hours the temperature of the thermostat bath was 30° C. and that of the crystal suspension of the acid was 31.9° C. The suspension was centrifuged (Sieva laboratory centrifuge, Hermle). 831 g of crystals and 1061 g of mother liquor were obtained (yield of 46%, calculated in terms of lactic acid). Some of the crystals from the crystallization were dissolved in water (90% solution) and the solution was analysed. The results are shown in the table below.

| | Crystallization |
|---|---|
| Colour (fresh) | 349 APHA |
| Colour (after hearing) | 713 APHA |
| Total nitrogen | 55 ppm |
| Total polysaccharides | 473 ppm |
| Total residual sugars | 430 ppm |
| Chiral purity | 99.97% |

An amount of 125 g of the crystals obtained above was melted in a microwave oven and the liquid was put into a short-path distiller (KDL-4). The conditions were as follows: oil bath temperature 120° C., feed rate 15 ml/min, pressure about 1 mbar, rotor speed 250 r.p.m., the cooling water was tap water.

94.4 g of distillate and 13.3 g of residue were obtained. The distillate was diluted with water until a 90% solution was obtained and this solution was analysed for colour. Colour (fresh): 6 APHA. Colour (after heating): 5 APHA.

The invention claimed is:

1. A method for the purification of an α-hydroxy acid on an industrial scale, comprising subjecting an α-hydroxy acid with a colour (fresh) of not more than 10,000 APHA units to (a) a crystallization step followed by (b) a distillation step.

2. The method according to claim 1, wherein the α-hydroxy acid is lactic acid or glycolic acid.

3. The method according to claim 2, wherein the α-hydroxy acid is lactic acid.

4. The method according to claim 1, wherein step (a) comprises two crystallization steps.

5. The method according to claim 4, wherein the crystallization steps are carried out in a cooling crystallization device, a melting crystallization device, an evaporative crystallization device and/or an adiabatic crystallization device.

6. The method according to claim 1, wherein step (a) is carried out in a cooling crystallization device, a melting crystallization device, an evaporative crystallization device and/or an adiabatic crystallization device.

7. The method according to claim 1, wherein the product stream from step (a) is separated into a mother liquor and α-hydroxy acid crystals by means of solid-liquid separation.

8. The method according to claim 1, wherein step (b) is carried out in one or more falling-film evaporators and/or thin-film evaporators and/or smeared film evaporators.

9. The method according to claim 1, wherein step (b) is carried out in a short-path distiller.

10. The method according to claim 7, wherein the separation comprises centrifugation or washing with one or more washing columns.

11. The method according to claim 2, wherein step (a) comprises two crystallization steps.

12. The method according to claim 3, wherein step (a) comprises two crystallization steps.

* * * * *